United States Patent
Rice et al.

(10) Patent No.: US 7,649,185 B2
(45) Date of Patent: Jan. 19, 2010

(54) FLUORESCENT PHANTOM DEVICE

(75) Inventors: Bradley W. Rice, Danville, CA (US); David G. Nilson, Walnut Creek, CA (US); Tamara L. Troy, San Francisco, CA (US)

(73) Assignee: Xenogen Corporation, Alameda, CA (US)

( * ) Notice: Subject to any disclaimer, the term of this patent is extended or adjusted under 35 U.S.C. 154(b) by 236 days.

(21) Appl. No.: 11/682,710

(22) Filed: Mar. 6, 2007

(65) Prior Publication Data

US 2007/0200058 A1     Aug. 30, 2007

Related U.S. Application Data

(63) Continuation-in-part of application No. 10/997,324, filed on Nov. 24, 2004, which is a continuation-in-part of application No. 10/068,573, filed on Feb. 6, 2002, now Pat. No. 6,919,919.

(51) Int. Cl.
  *G01J 1/58*   (2006.01)
  *A61B 6/00*   (2006.01)
  *G12B 13/00*  (2006.01)

(52) U.S. Cl. ............... 250/458.1; 600/476; 600/478; 250/252.1

(58) Field of Classification Search .......... 250/458.1, 250/459.1, 252.1; 600/476, 478
See application file for complete search history.

(56) References Cited

U.S. PATENT DOCUMENTS

| | | | |
|---|---|---|---|
| 4,196,994 A | 4/1980 | de Jesus et al. | |
| 4,727,247 A | 2/1988 | Johnston | |
| 4,948,975 A | 8/1990 | Erwin et al. | |
| 5,008,548 A | 4/1991 | Gat | |
| 5,060,061 A | 10/1991 | Shishido et al. | |
| RE33,973 E | 6/1992 | Kriz et al. | |
| 5,130,794 A | 7/1992 | Ritchey | |
| 5,202,091 A | 4/1993 | Lisenbee | |
| 5,272,518 A | 12/1993 | Vincent | |
| 5,319,209 A | 6/1994 | Miyakawa et al. | |
| 5,414,258 A | 5/1995 | Liang | |

(Continued)

FOREIGN PATENT DOCUMENTS

EP     0 228 877     7/1987

(Continued)

OTHER PUBLICATIONS

European Search Report dated Feb. 5, 2008 from EP Application No. 02742268.2 (5 pages).

(Continued)

*Primary Examiner*—David P Porta
*Assistant Examiner*—Faye Boosalis
(74) *Attorney, Agent, or Firm*—Beyer Law Group LLP

(57) ABSTRACT

Described herein is a phantom device that simplifies usage, testing, and development of light imaging systems. The phantom device includes a body and a fluorescent light source internal to the body. The body comprises an optical material designed to at least partially resemble the optical behavior of mammalian tissue. The phantom device has many uses. One use of the phantom device permits testing of tomography software in the imaging system, such as software configured for 3D reconstruction of the fluorescent light source. Another use tests spectral unmixing software in the imaging system. The phantom device also allows a user to compare trans- and epi-fluorescent illumination imaging results.

35 Claims, 10 Drawing Sheets

U.S. PATENT DOCUMENTS

| | | | |
|---|---|---|---|
| 5,515,161 A | 5/1996 | Blumenfeld | |
| 5,587,583 A | 12/1996 | Chin et al. | |
| 5,636,299 A | 6/1997 | Bueno et al. | |
| 5,637,874 A | 6/1997 | Honzawa et al. | |
| 5,650,135 A | 7/1997 | Contag et al. | |
| 5,672,881 A | 9/1997 | Striepeke et al. | |
| 5,689,110 A | 11/1997 | Dietz et al. | |
| 5,705,807 A | 1/1998 | Throngnumchai et al. | |
| 5,738,101 A | 4/1998 | Sappey | |
| 5,840,572 A | 11/1998 | Copeland et al. | |
| 5,865,754 A * | 2/1999 | Sevick-Muraca et al. | 600/476 |
| 5,867,250 A | 2/1999 | Baron | |
| 5,883,830 A | 3/1999 | Hirt et al. | |
| 5,970,164 A | 10/1999 | Bamberger et al. | |
| 6,205,244 B1 | 3/2001 | Bawolek et al. | |
| 6,217,847 B1 | 4/2001 | Contag et al. | |
| 6,242,743 B1 | 6/2001 | DeVito et al. | |
| 6,321,111 B1 | 11/2001 | Perelman et al. | |
| 6,364,829 B1 | 4/2002 | Fulghum | |
| 6,381,058 B2 | 4/2002 | Ramm | |
| 6,597,439 B1 | 7/2003 | Hakamata | |
| 6,615,063 B1 | 9/2003 | Ntziachristos et al. | |
| 6,642,953 B1 | 11/2003 | Nieto Velasco et al. | |
| 6,759,814 B2 | 7/2004 | Vogel et al. | |
| 6,775,567 B2 | 8/2004 | Cable et al. | |
| 6,919,919 B2 | 7/2005 | Nelson et al. | |
| 6,922,246 B2 | 7/2005 | Nilson | |
| 7,116,354 B2 | 10/2006 | Rice et al. | |
| 7,331,673 B2 | 2/2008 | Ono | |
| 7,482,167 B2 | 1/2009 | Sammak et al. | |
| 2001/0028510 A1 | 10/2001 | Ramm et al. | |
| 2003/0036860 A1 | 2/2003 | Rice et al. | |
| 2003/0156194 A1 | 8/2003 | Sugiura et al. | |
| 2005/0145786 A1 | 7/2005 | Rice et al. | |
| 2007/0013780 A1 | 1/2007 | Rice et al. | |

FOREIGN PATENT DOCUMENTS

| | | |
|---|---|---|
| EP | 0 491 131 | 6/1992 |
| EP | 0656731 | 6/1995 |
| FR | 2 802 009 | 6/2001 |
| WO | WO 94/00742 | 1/1994 |
| WO | WO 00/17643 | 3/2000 |

OTHER PUBLICATIONS

Dynex Technologies, Inc., website, A Thermo BioAnalysis Company "Dynex Microplates", http://www.dynextechnologies.com/index.html, printed Apr. 19, 2002.

Integrated Photomatrix Limited, "Closed Loop Control", Dorset, England, available Dec. 1, 2001.

Labsphere, website http://labsphere.com , printed Apr. 19, 2002.

Lambda Research Corporation, website, http://lambdares.com , printed Apr. 19, 2002.

Optronic Laboratories, Inc., website, Manufacturer of Light Measurement Instrumentation, Standards, http://olinet.com, printed Apr. 19, 2002.

Prahl, Scott. "Optical Phantoms," http://omlc.ogi.edu/classroom/phantom/index.html, 1998, printed Jul. 18, 2007.

Vernon, Marcia L. et al., "Fabrication and characterization of a solid polyurethane phantom for optical imaging through scattering media," Applied Optics, vol. 38, No. 19, pp. 4247-4251, Jul. 1, 1999.

Hamamatsu Corporation, USA, website, http://usa.hamamatusu.com/ pp. 1-4, Apr. 27, 2001, printed Apr. 27, 2001.

Hamamatsu, Imaging Box Instruction Manual, 55310-224-1, Nov. 2000.

Mahmood, U. et al., "Near-Infrared Optical Imaging of Protease Activity for Tumor Detection", Radiology 1999, 213, pp. 866-870.

Weissleder, R. et al., "Shedding Light onto Live Molecular Targets", Nature Medicine, Jan. 2003, vol. 9, No. 1, pp. 123-128.

Office action dated Jan. 8, 2009 from U.S. Appl. No. 11/523,480.

Summons to Attend Oral Proceedings dated May 8, 2009 for European Application No. 02742268.2.

International Search Report dated May 28, 2009 in PCT Application No. PCT/US08/55965.

Written Opinion dated May 28, 2009 in PCT Application No. PCT/US08/55965.

Office Action dated Jun. 24, 2009 in U.S. Appl. No. 11/523,480.

* cited by examiner

FLUORESCENT PHANTOM DEVICE

CROSS-REFERENCE TO RELATED APPLICATIONS

This application claims priority under 35 U.S.C. §120 and is a continuation-in-part of U.S. patent application Ser. No. 10/997,324, filed Nov. 24, 2004 and titled "TISSUE PHANTOM CALIBRATION DEVICE FOR LOW LEVEL LIGHT IMAGING SYSTEMS," which is incorporated herein by reference for all purposes, and which claimed priority under 35 U.S.C. §120 from U.S. patent application Ser. No. 10/068,573 (now U.S. Pat. No. 6,919,919), filed Feb. 6, 2002 and titled "Light Calibration Device for Use in Low Level Light Imaging Systems," which is also incorporated herein by reference for all purposes.

FIELD OF THE INVENTION

The present invention generally relates to light imaging. More specifically, the present invention relates to tissue phantom devices that include a fluorescent light source.

BACKGROUND

Imaging with light is gaining popularity. One type of light imaging involves the capture of low intensity light from a biological sample. A source of the light indicates a portion of the sample where an activity of interest may be taking place. In one example, the sample is a small animal such as a mouse and the light source could be tumor cells labeled with light emitting reporters such as firefly luciferase or fluorescent proteins or dyes. This technology is known as in vivo optical imaging.

Detection of light-emitting probes in-vivo within small living animals relies on the semitransparent nature of mammalian tissue, and requires complex instrumentation such as a high-sensitivity low-noise camera and advanced imaging software tools to interpret an image. The propagation of light through tissue is a diffusive process and therefore depends on the scattering and absorption properties of tissue. Complex computer routines can localize a source of light in three-dimensions in tissue by simulating the photon diffusion process. This technique is often referred to as diffuse imaging tomography. Testing and development of such software often employs a living specimen, such as a real mouse, to verify accurate software results. In addition, purchasers of an imaging system often train new users on the system and/or software to build user familiarity. However, a living mouse is not an ideal subject for these instances. Careful handling requirements and the need for anesthesia make living mammals non-ideal for software development, software testing, and personnel training.

SUMMARY

The present invention relates to a phantom device that simplifies usage, testing, and development of light imaging systems. The phantom device includes a body and a fluorescent light source internal to the body. The body comprises an optical material designed to at least partially resemble the optical behavior of mammalian tissue.

The phantom device has many uses. Imaging the fluorescent light source or phantom device may incorporate known properties of the optical material, fluorescent light source and/or phantom device. After imaging, comparisons may be made between a) the imaging results and b) known results for the optical material, fluorescent light source and/or phantom device. The comparison results may then be used to assess functional integrity of one or more components in the imaging system. The assessment may build a digital representation of the light source or phantom device and compare one or more components of the digital representation against one or more known properties for the light source or the phantom device.

One use of the phantom device permits testing of tomography software in the imaging system, such as software configured for 3D reconstruction of the fluorescent light source. Another use tests spectral unmixing software in the imaging system, which separates different fluorophore spectra. The phantom device also allows a user to compare trans- and epi-fluorescent illumination imaging results.

In one aspect, the present invention relates to a phantom device. The phantom device includes a body and a fluorescent light source. The body includes one or more surfaces and an optical material designed to at least partially resemble the optical behavior of mammalian tissue. The fluorescent light source is disposed within the body and configured to emit fluorescent light from within the body, through the optical material and to the one or more surfaces.

In another aspect, the present invention relates to a phantom device for use with a light imaging system. The phantom device includes a body, one or more holes in the body, a removable member, and a fluorescent light source. The body includes one or more surfaces and an optical material designed to at least partially resemble the optical behavior of mammalian tissue. The removable member includes a cavity and is shaped to fit in the hole. The fluorescent light source is disposed in the cavity and configured to emit fluorescent light from within the body when the removable member is in the hole.

In yet another aspect, the present invention relates to a method for testing a light imaging system. The method includes receiving a phantom device, where the phantom device comprises a body that includes an optical material designed to at least partially resemble the optical behavior of mammalian tissue and a fluorescent light source internal to the body. The method also includes illuminating the body with excitation light that causes the fluorescent source to emit fluorescent light. The method further includes capturing an image of at least a portion of a phantom device. The method additionally includes building a digital representation of the fluorescent light source using data included in the image. The method also includes comparing a component of the digital representation to a known property for the fluorescent light source or the phantom device.

In still another aspect, the present invention relates to a computer readable medium including instructions for testing a light imaging system.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, components, and designs have not been described in detail so as not to unnecessarily obscure aspects of the present invention.

Described herein are tissue phantom devices for use with a light imaging system. A tissue phantom device is an inanimate device that simulates the diffusion of photons through mammalian tissue. The phantom device includes an internal fluorescent light source. When imaged, the fluorescent light source often causes the device—or portions thereof—to glow or emit light from a surface, hence the term 'phantom'. As the term is used herein, 'test device', 'phantom device' and 'tissue phantom' are used interchangeably and all relate to a device used in an imaging system that includes an internal light source.

First, with respect to FIGS. 1-6, this disclosure describes phantom devices. Each phantom device permits, for example, benchmarking of diffuse tomographic imaging systems and software. These and other uses and methods for using a phantom device are described further with respect to FIGS. 8-10. FIGS. 7A and 7B illustrate an imaging system 10 suitable for internally receiving and imaging a phantom device.

Figure 1:
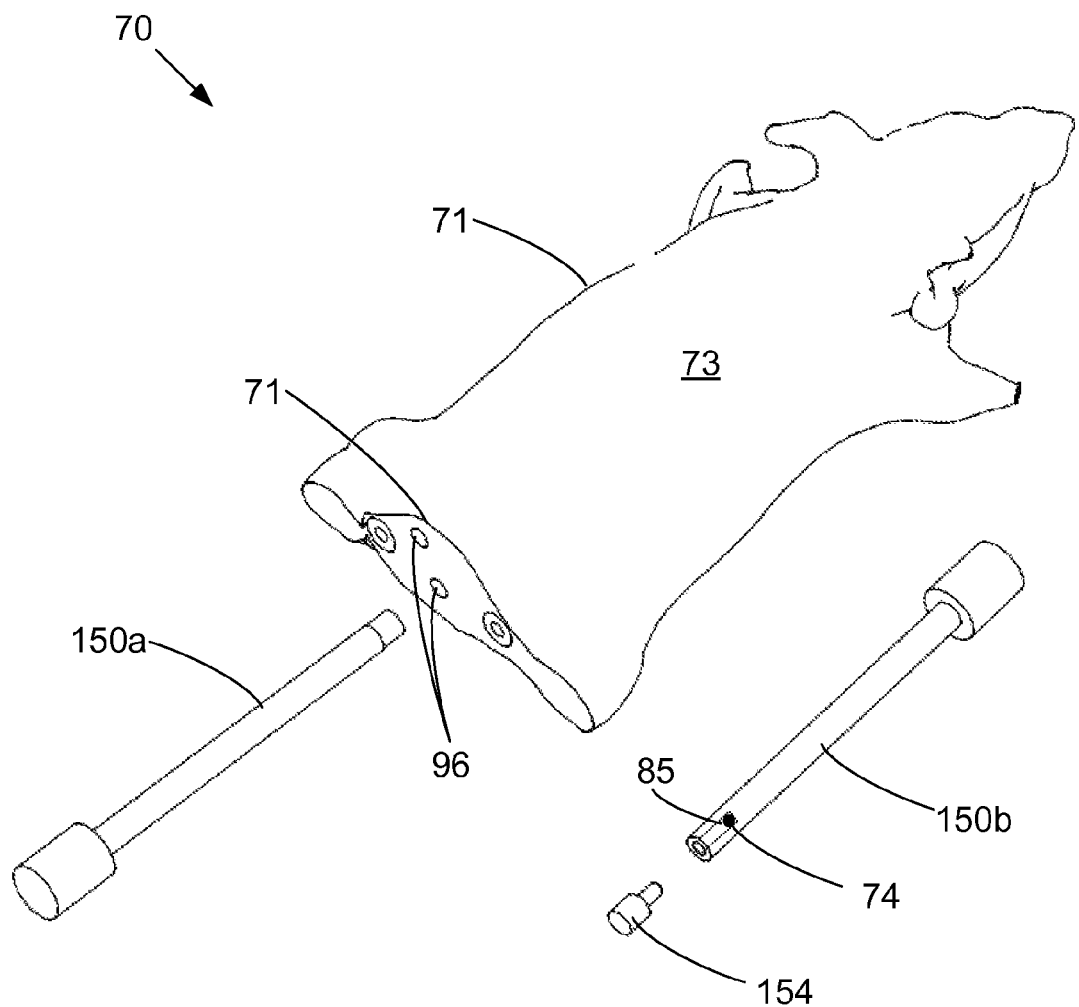
FIG. 1 illustrates an exploded perspective view of components in a phantom device in accordance with one embodiment of the present invention.
Figure 2A:
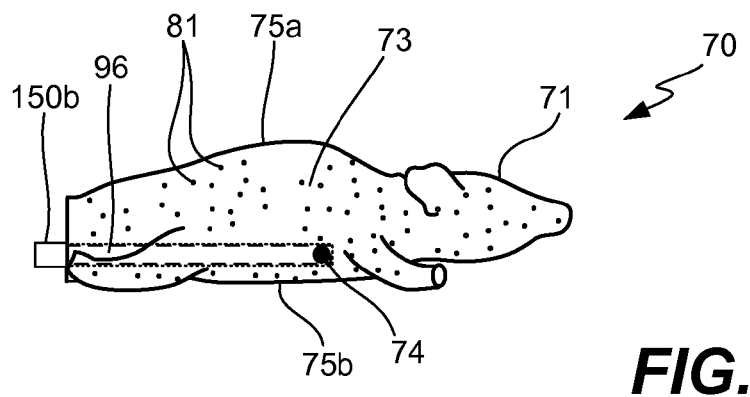
FIGS. 2A-2C illustrate different views of a phantom device in accordance with one embodiment of the present invention.
Figure 2B:
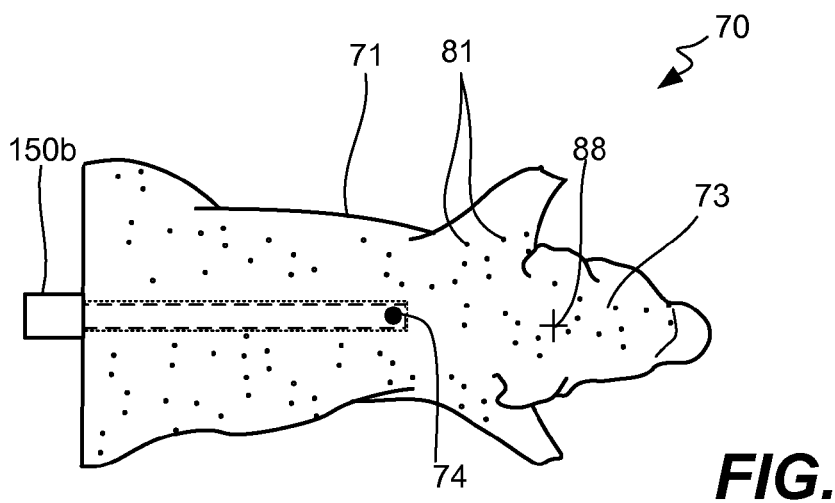
Figure 2C:
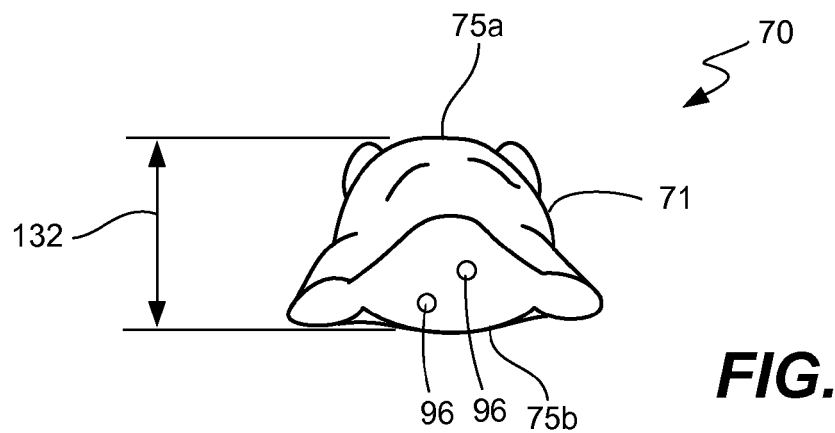

FIG. 1 illustrates an exploded perspective view of components in a phantom device 70 in accordance with one embodiment of the present invention. FIGS. 2A-2C illustrate different views of phantom device 70.

As shown in FIG. 1, phantom device 70 includes a main body 71 and one or more removable members 150 for insertion into holes 96 in body 150. A fluorescent light source 74 is disposed in a cavity 85 in removable member 150 for insertion into body 71. Fluorescent light source 74 will be described in further detail after body 71 is first expanded upon.

Phantom device 70 simulates the diffusion of photons through mammalian tissue. In one embodiment, both body 71 and removable members 150 both include an optical material 73. This provides a phantom device 70 with homogenous optical properties, despite having multiple components that make up its volume.

Optical material 73 (or 'optically selective material') is designed and configured to at least partially resemble the optical behavior of mammalian tissue. Mammalian tissue acts as a turbid medium that scatters photons, absorbs photons, and autofluoresces. Optical material 73 may be designed and configured to resemble one or more of these optical properties. For phantom device 70, optical material 73 resembles three optical properties of mammalian tissue: autofluorescence, optical absorption, and optical scattering.

Optical material 73 resembles the optical autofluorescence properties of mammalian tissue. Autofluorescence refers to the natural fluorescence of substances within a material or organism. Mammalian tissue, and the body 71 in phantom device 70, both have autofluorescence properties that will affect fluorescent imaging. A camera usually receives image data that includes—and mixes—the autofluorescence of body 71 (or tissue in a real mammal) with the spectra of light source 74. Spectral unmixing software in an imaging system separates these two (see FIG. 10) so that fluorescence of light source 74 can be processed separately for tomographic assessment, without the noise and contributions of autofluorescence from the mammalian tissue or body 71 in phantom device 70.

Figure 6:
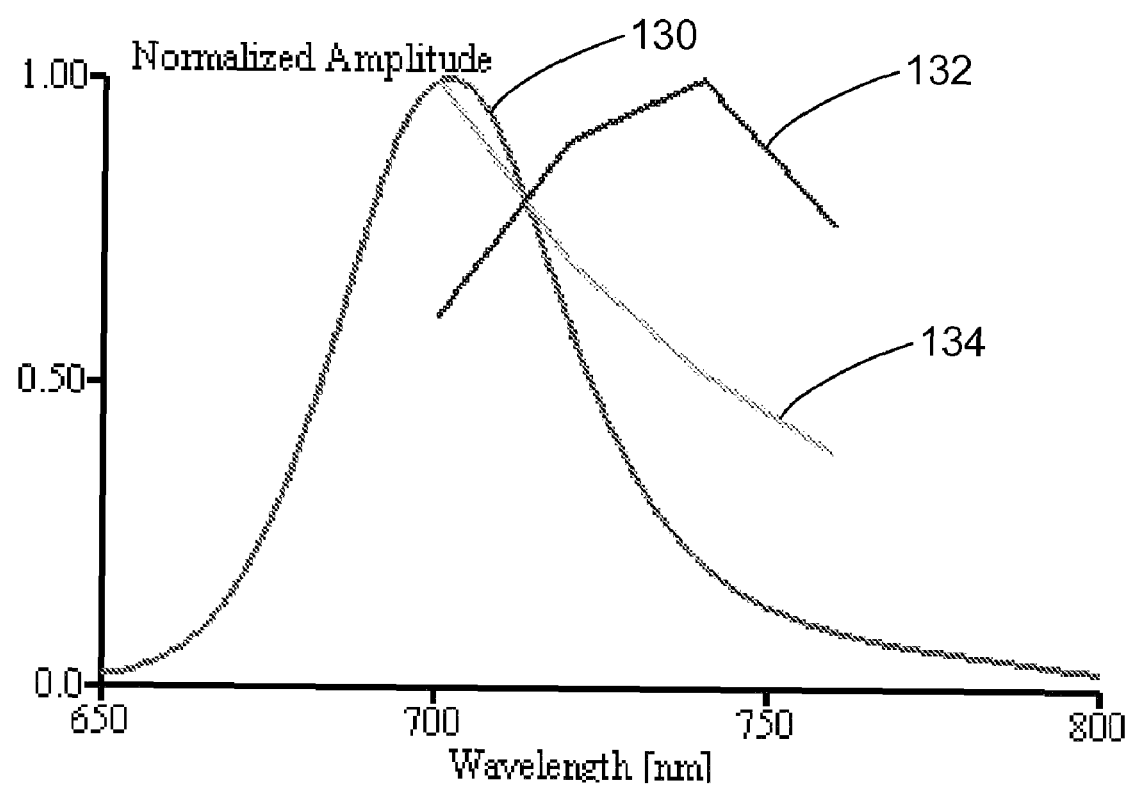
FIG. 6 illustrates an exemplary spectral output for a phantom device in accordance with a specific embodiment of the present invention.
Figure 7A:
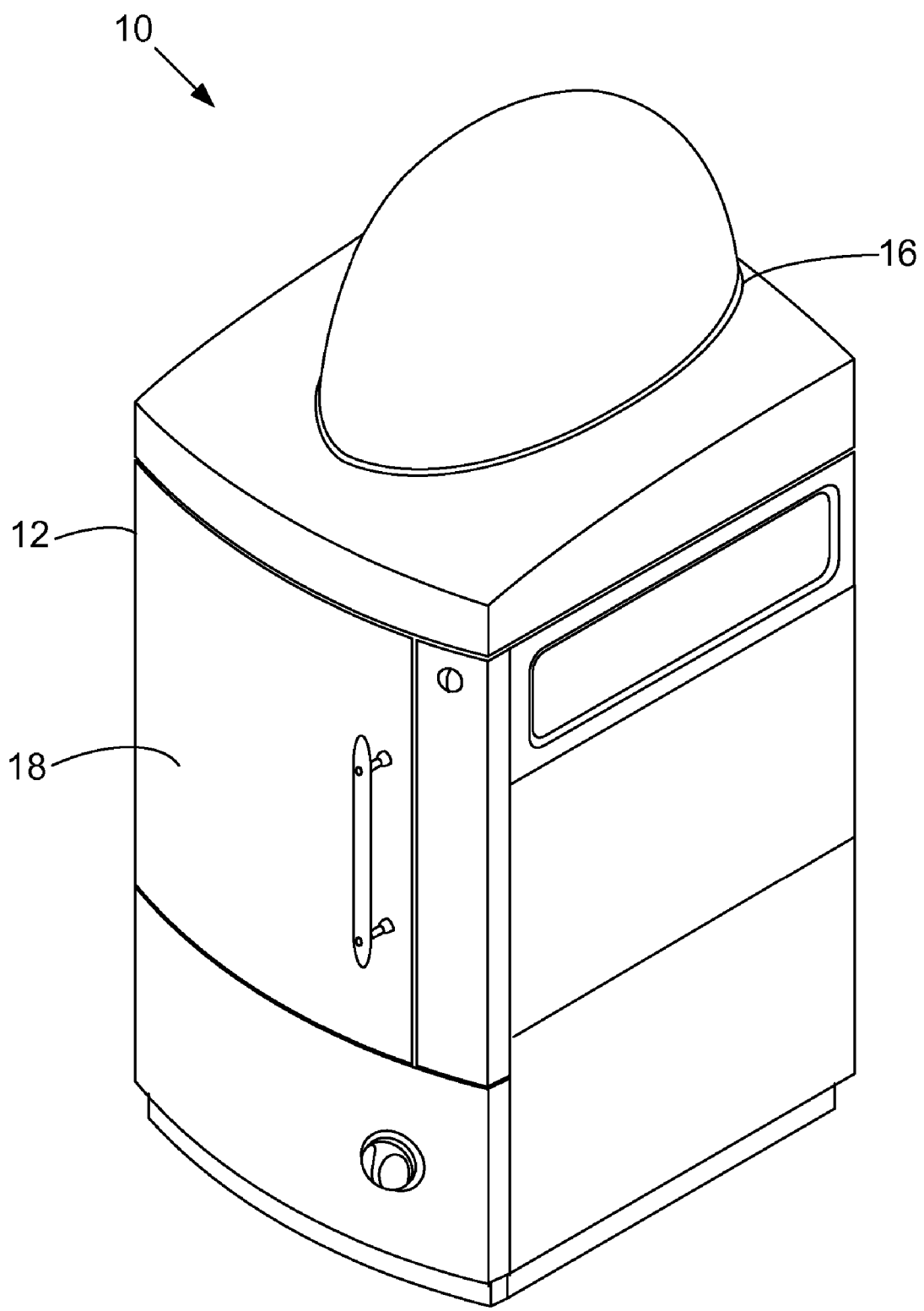
FIGS. 7A and 7B illustrate a perspective view of an imaging system in accordance with one embodiment of the present invention.
Figure 7B:
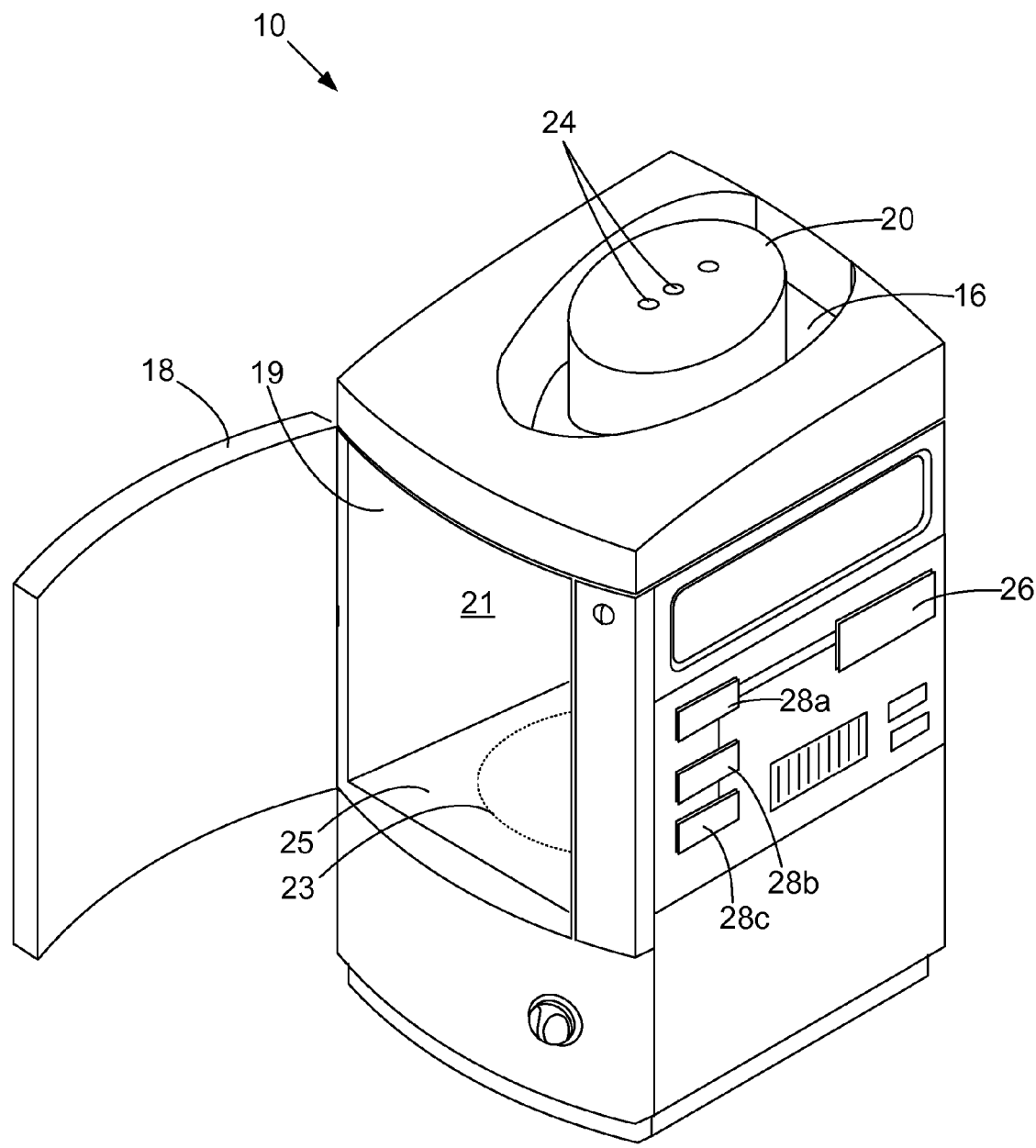

Spectrum 134 in FIG. 6 corresponds to the autofluorescence of body 71 in phantom device 70. Spectrum 134 substantially resembles the autofluorescence of mammalian tissue. In one embodiment, spectrum 134 is achieved using a polymer and reddish dye for body 71 that together include an autofluorescence that resembles mammalian tissue. Values for spectrum 134 may be stored for imaging system assessment; other spectra are suitable for use.

Optical material 73 also resembles the optical absorption properties of mammalian tissue. Tissue absorption in living mammals is generally affected by the presence of hemoglobin, which absorbs light significantly in the blue-green region of the visible spectrum and is relatively transparent in the red wavelengths greater than 600 nanometers. In a specific embodiment, optical material 73 comprises a polyurethane base with a reddish dye that absorbs light significantly in the blue-green region and is relatively transparent in a red region of the visible spectrum. One dye suitable for use with the present invention is Disperse Red 1 as provided by Sigma-Aldrich of St. Louis, Mo. One suitable mixture includes a dye solution consisting of 124 mg of disperse red dye to 91 ml ethyl alcohol. The ratio of dye solution to polyurethane may range from about 0.001 ml/gm to about 0.02 ml/gm. In a specific embodiment, the ratio of dye solution to polyurethane is about 0.0104 ml/gm. It is understood that different dyes and different amounts of a particular dye may be used with a polymer to achieve a desired absorption spectrum.

Figure 4:
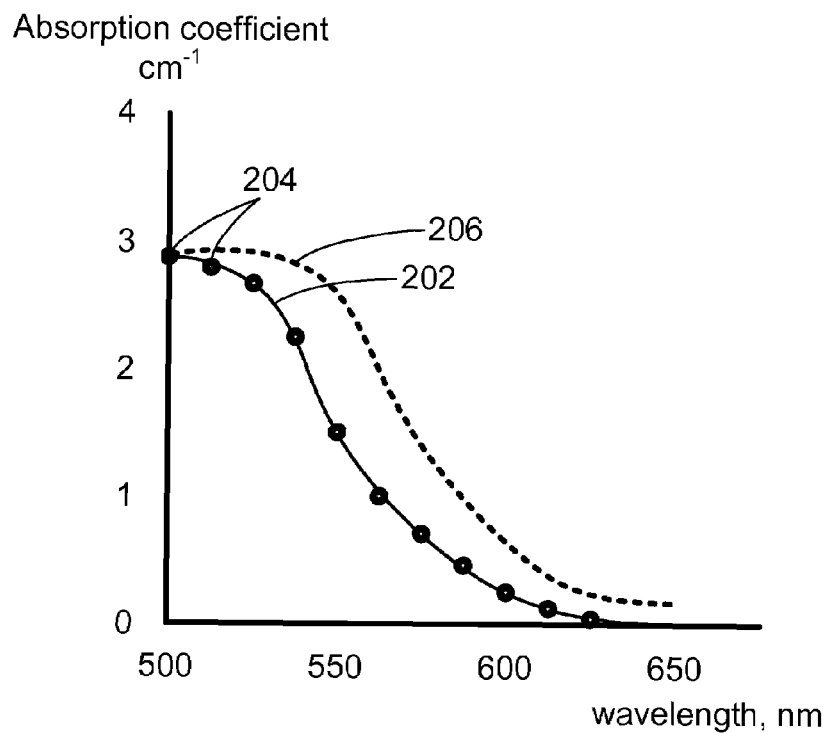
FIG. 4 illustrates an exemplary absorption coefficient curve for different wavelengths in accordance with a specific embodiment of the present invention.

Spectral absorption characteristics of mammalian tissue in the visible spectrum may be used to determine how optical material 73 is dyed at multiple wavelength points in the visible spectrum. FIG. 4 illustrates an exemplary absorption coefficient curve 202 for optical material 73 for different wavelengths in the visible spectrum. Absorption curve 206 approximates the absorption performance of mammalian tissue. Absorption coefficient curve 202 mimics curve 206, and corresponds to the absorption characteristics of optical material 73. Individual points 204 on curve 202 represent coefficients of absorption at a specific wavelength. Each point 204 is stored in memory and applied during reconstruction of an internal light source for an image taken of phantom device 70 at a corresponding wavelength. Image capture and light source software reconstruction at different wavelengths may then proceed with known absorption characteristics of material 73 at each wavelength. Absorption coefficient curve 202 thus allows spectral imaging and fluorescent unmixing at multiple wavelengths that resembles mammalian tissue across the visible spectrum.

Figure 5:
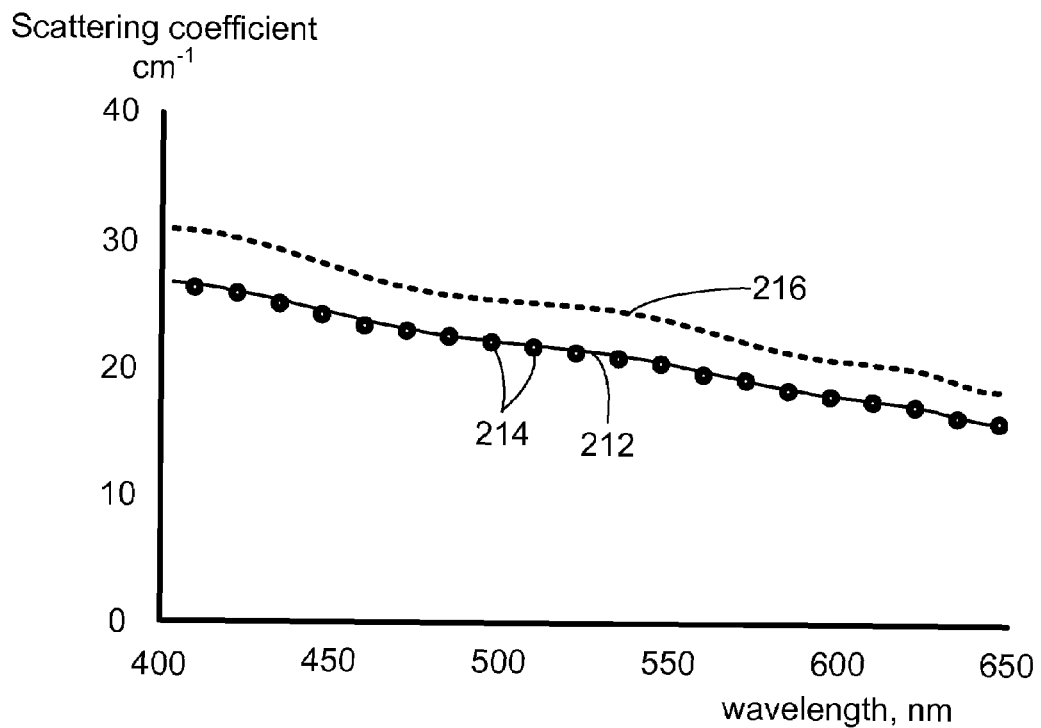
FIG. 5 illustrates an exemplary scattering coefficient curve for different wavelengths in accordance with a specific embodiment of the present invention.

Optical material 73 is also designed and configured to resemble an optical scattering property of mammalian tissue. For wavelengths greater than 600 nanometers, the scattering coefficient of mammalian tissue is about 20 cm$^{-1}$, which corresponds to an effective length for scattering of about 0.05 cm. In a regime where scattering is pronounced, a significant amount of light can escape tissue of a living mammal, but the emission is often highly diffuse. FIG. 5 illustrates one suitable representative scattering coefficient curve 212 for material 73, which is stored in memory for different wavelengths in the visible spectrum, in accordance with a specific embodiment of optical material 73. Scattering coefficient curve 216 approximates the scattering performance of mammalian tissue. Individual points 214 on curve 212 represent coefficients of optical scattering at a specific wavelength for material 73. Image capture and light source reconstruction at different wavelengths may then proceed with known optical scattering characteristics of material 73 at each wavelength. Each point 214 is stored in memory and applied during reconstruction of an internal light source for an image taken of phantom device 70 with a corresponding wavelength. Scattering curve 202 thus allows spectral imaging at multiple wavelengths that resembles varying spectral scattering characteristics of mammalian tissue.

In a specific embodiment, optical material 73 comprises one or more scattering particles 81 (FIGS. 2A and 2B) to help material 73 resemble the optical scattering nature of mammalian tissue. Material 73 is then particulated such that its curve 216 resembles curve 212 and the actual optical scattering characteristics of mammalian tissue in the visible wavelength range. The type of scattering particle and amount disposed within material 73 may be varied according to a desired degree of scattering within phantom device 70. Many suitable scattering particles will not be visible to the human eye (but are shown in the Figures for sake of illustration). One suitable scattering particle comprises titanium dioxide ($TiO_2$), for example, which is added to a polymer precursor before polymerization to subsequently form material 73. In one embodiment, the ratio of titanium dioxide beads to polyurethane is from about 0.002 gm/gm to about 0.003 gm/gm. In a specific embodiment, the ratio of titanium dioxide beads to polyurethane is about 0.0026 gm/gm. Other scattering particles and concentrations are also suitable for use. The amount of scattering particles 81 added to optical material 73 may be tailored according to optical scattering property of mammalian tissue. Similar to spectral absorption, the optical scattering characteristics of mammalian tissue 216 may be used to determine how optical material 73 is particulated at multiple wavelength points in the visible spectrum. Typically, as shown by 216, scattering decreases with increasing wavelength in the visible spectrum for mammalian tissue. Correspondingly, material 73 may include optical scattering characteristics that decrease and mimic mammalian tissue in the visible wavelength range.

In FIG. 2A, body 71 also provides mechanical integrity for device 70 and protects optical components contained therein. In this case, material 72 used in body 71 includes a suitable rigidity to resist forces associated with usage, such as handling. In a specific embodiment, body 71 comprises polyurethane alloyed to obtain one or more optical properties. Other polymers and materials are suitable for use.

In one embodiment, optical material 73 is substantially homogeneous and included in both body 71 and any removable members 150. It is understood that real animals are not homogeneous and that tissue absorption for living mammals varies with the type of tissue or tissue cells, and is generally affected by varying particles and quantities such as the presence of hemoglobin. However, software run by imaging system 10 may implement homogeneous assumptions on the optical behavior of mammalian tissue when imaging a living mouse. The software may also implement the same homogeneous assumptions when imaging phantom device 70 and optical material 73. To facilitate testing of software configured with such assumptions, optical material 73 may then comprise a substantially homogeneous composition. This may be achieved during manufacture of body 71 by mixing polymer precursors and optical additives inserted therein to achieve consistency throughout the precursor before polymerization. In addition, polymerization of the precursor may be controlled to minimize the formation of voids and other optical impurities in body 71.

In another embodiment, body 71 is heterogeneous and includes at least two different materials. This may include heterogeneous phantom devices not manufactured to achieve homogeneous composition and/or phantom devices constructed from multiple parts having different optical properties. For example, body may include a) an upper portion of device 70 that is constructed to diffuse and scatter light as described for material 73 and b) a non-optical lower portion. When the device 70 is imaged using a camera disposed above the device, the non-optical lower portion may not greatly affect device imaging. Body 71 may also include parts attached thereto that also create a heterogeneous structure. For example, the back side of body 71 may be opaque. Alternatively, removable members 150 may comprise a material different from body 71 that creates a heterogeneous structure. Other heterogeneous configurations and inclusions are contemplated.

Body 71 includes one or more surfaces 75. The number of surfaces 75 will depend on the configuration of phantom device 70. Frequently, phantom device 70 comprises a bottom surface 75b that is substantially flat and allows phantom device to be readily rested on a flat surface. The number and shape of other surfaces will depend on the shape chosen for phantom device 70. In one embodiment, phantom device 70 resembles a mammal. For FIGS. 1-2C, body 71 comprises a shape that resembles a mouse with distal portions for the arms and legs omitted. In this case, casting a polymer precursor in a mold dimensioned to resemble a mouse may form test device 70 and define all surfaces 75.

Other surface topographies may be used. The test device 100 of FIG. 3 comprises a trapezoidal geometry in accordance with a specific embodiment of the present invention. In this case, testing device 100 comprises six surfaces 105 shaped to form an extended frustum. Testing device 100 is machined to include surfaces 105 of known dimensions, which simplifies imaging and measuring surface topography for device 100. In this case, verification of software using phantom device 100 may rely on known dimensions for each surface of testing device 100.

Figure 3:
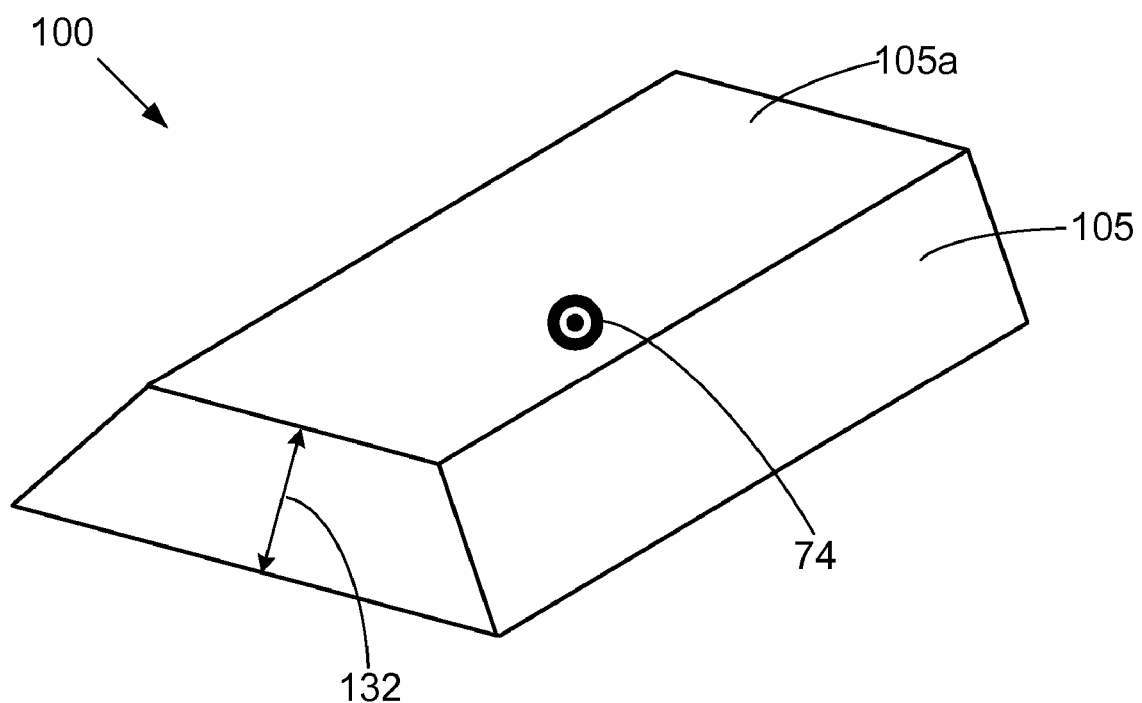
FIG. 3 illustrates a testing device that includes a trapezoidal shape in accordance with a specific embodiment of the present invention.

Height 132 is defined as the distance from the bottom surface 75b to the topmost surface 75a and 105a (FIGS. 2C and 3). In one embodiment, height 132 is configured relative to the depth of field of focus of an imaging system that phantom device 70 is used with. Alternately, height 132 may be designed to resemble the height of a mammal to be imaged.

A test device having a height between about 10 mm to about 40 mm is suitable for many imaging systems. In a specific embodiment, height 132 is about 20 mm, which corresponds to the average height of a mouse commonly used in imaging applications.

Phantom device 70 may also include a fiducial mark 88 (FIG. 2B) that serves as a spatial reference when imaging phantom device 70. Thus, software implemented by imaging system 10 may compare a) a reconstructed location of light source 74 relative to fiducial mark 88 with b) a known location light source 74 relative to fiducial mark 88 (e.g., does a=b?).

In one embodiment, phantom device 70 is constructed using conventional plastics fabrication techniques. Additional fabrication steps may be implemented to achieve one more optical properties custom to phantom device 70. For example, a vacuum pump may be used to withdraw and remove air bubbles from a polymer mixture during fabrication to further increase the homogeneous nature of body material 71. In addition, ultrasonic energy may be used to break up titanium dioxide beads into smaller particles than those commercially available and increase homogeneous composition of body material 71. In a specific embodiment, body material 71 is made according to the following procedure. Commercially available polyurethane precursors are obtained and separated into two parts: part A and part B. Ethyl alcohol is added to a dye powder and about 7.5 ml of the solution is mixed with about 70 g of polyurethane part B. About 1.95 g of titanium dioxide beads are added to the solution and stirred. The solution is then placed into an ultrasonic cleaner with about 1 quart of water as a cleaner. Ultrasonic energy is then applied for about seven to eight minutes to break up the titanium dioxide, avoid formation of any clumps, and provide uniformly distributed mixture. About 274 g of polyurethane part B are then added and the mixture is stirred. About 100 g of polyurethane part A is added to about 85 g of the mixture previously developed, and the combination is again stirred. The preformed polymer is then placed in a vacuum for about 15 to about 60 seconds to withdraw and remove air bubbles from a polymer mixture. The preformed polymer is then poured into a suitably shaped mold for body 71 and removable members 150 and cured under pressure. In one embodiment, a mouse shaped mold for body 71 is obtained by freezing a dead mouse to create a detailed dimension mold.

Fluorescent light source 74 is stored in a cavity 85 within the volume of device 70. In one embodiment, cavity 85 is included in body 71. In another embodiment, and as shown, cavity 85 is included in a removable member 150*b*, which is configured for manual insertion into body 71. Cavity 85 includes a volume that is suitably sized according to the amount of fluorescent light source 74 contained therein.

Device 70 includes two removable members 150*a* and 150*b*. Removable member 150*b* includes a cavity 85 that contains fluorescent light source 74. Removable member 150*a* does not include a cavity 85—and functions to fill any holes 96 that do not include a removable member 150*b* and a fluorescent light source so as to maintain a homogeneous internal volume for phantom device 70. Removable member 150*b* may or may not have a cavity 85.

Each removable member 150 has a cylindrical shape, resembling a rod, and is sized to fit into a hole 96, which provides access to central volumetric portion of body 71 (see FIGS. 2A and 2B). More specifically, hole 96 and removable member 150 are dimensioned such that: removable member 150 a) press fits into hole 96 to minimize escape of light along the interface between removable member 150 and hole 96, and b) hole 96 and removable member 150 permit manual removal and insertion of removable member 150 within hole 96.

As mentioned above, removable member 150 includes the same optical material as body 71. This reduces optical effects of removable member 150 when imaging device 70 and maintains the homogeneous optical nature of device 70. When the optical material comprises a plastic or polyurethane base, this allows removable member 150 and hole 96 to be machined to press fit dimensions to further reduce light escape along an interface between removable member 150 and hole 96.

Removable member 150*b* provides several functions for phantom device 70. First, removable member 150*b* permits a user to insert, and withdraw, fluorescent light source 74 into, and from, body 71. As shown in FIG. 1, fluorescent light source 74 is embedded in a cavity 85 at a distal end of the cylindrical removable member 150. A cap 154 includes a plug that inserts and press fits into cavity 85 at the distal end of removable member 150*b*—but leaves enough volume in cavity 85 for the fluorescent light source 74. For example, cavity 85 may have a cylindrical depth of about 4 millimeters while the plug extends about 4 millimeters into the cavity. Other dimensions may be used. The plug may be glued or otherwise attached and sealed into place to prevent fluorescent light source 74 escape. Removable member 150*b* thus permits mechanical insertion and removal of fluorescent light source 74 deep within body 71 according to the sizing of removable member 150.

Device 70 may include multiple holes 96, which provides a second function for removable member 150*b*: it allows a user to manually change the position of fluorescent light source 74 in body 71. In this manner, phantom device 70 includes multiple positions for fluorescent light source 74. Each of these positions may be stored in software for calibration and testing purposes. The two holes 96 can be vertically offset (FIG. 1), laterally offset, or a combination thereof (FIG. 2C). Vertical offset facilitates assessment and comparison of trans- and epi-fluorescent illumination. Other holes 96 may be included to position light source in other locations in body 71.

Device 70 may comprise multiple fluorescent light sources 74 and/or multiple holes 96. For example, two removable members 150 may be used for insertion into two holes 96 (FIGS. 1 and 2C). The fluorescent light sources 74 may include the same fluorescent light source spectrum or material, or different ones. This provides a third function for removable member 150*b*: it allows a user to change the fluorescent light source used in device 70. Three or more fluorescent light sources 74 are also suitable. In a specific embodiment, phantom device 70 is sold or provided with 6 removable members 150*b* that each have a different fluorescent light source 74. A device may also use less light sources 74 than it has holes 96 when there are multiple holes 96. In this case, removable member 150*a* is inserted into the holes 96 not currently including a removable member 150*b*. FIGS. 2A and 2B show device 70 with only a single hole 96.

Fluorescent light source 74 generally refers to any object or molecule that produces fluorescent light. Fluorescent light source 74 typically absorbs incident energy of a certain wavelength or wavelength range and, in response, emits light energy at a different wavelength or wavelength range. The absorption of light is often referred to as the "excitation", while the emission of longer wave lights as the "emission". The output wavelength range is referred to herein as an 'output sepctrum'. Fluorescent light source 74 may include one or more fluorescent light emitting molecules, called 'flourophores'. A flourophore refers to a molecule or a functional group in a molecule that absorbs energy of a specific wavelength and re-emits energy at a different wavelength. Many commercially available fluorophores are suitable for use with device 70. Suitable fluorophores include indocyanide green, quantum dot 605, quantum dot 800, AlexaFluor™ 680 and AlexaFluor™ 750 as provided by Invitrogen of San Diego, Calif. The fluorophore may be stored in a solution, such as alcohol or saline, in cavity 85. In one embodiment, fluorescent light source 74 includes the same fluorescent molecules or emitters used in imaging in a living animal subject, and thus emits a light spectrum that resembles a fluorescent biological reporter used in the living animal subject. Both organic and inorganic substances can exhibit fluorescent properties, and are suitable for use with fluorescent light source 74.

When excited by suitable incident light, fluorescent light source 74 emits fluorescent light from within phantom device 70. The light then travels through optical material 73 to one or more surfaces of device 70, where it may be detected by a camera.

In general, fluorescent light source 74 emits light in the range of about 400 nanometers to about 1300 nanometers. Within this range, fluorescent light source 74 and/or optical material 73 may be configured or combined to emit light from device 70 according to a particular spectral curve or spectral output.

FIG. 6 illustrates a sample spectral output for components in phantom device 70 in accordance with a specific embodiment of phantom device 70. In this case, fluorescent light source 74 is configured to emit a spectrum 130. Spectrum 130 permits spectral differences in absorbance of optical material 73 to help determine the location of light source 74 within body 71 using multiple wavelengths and spectral unmixing. The spectral unmixing may also be used to distinguish removable members 150 from body 71. As shown, spectral unmixing (see FIG. 6) of the light detected from tissue phantom produces light curves 132 and 134 for removable members 150 and body 71, respectively. These known results for spectral unmixing of device 70 may be stored to test spectral unmixing software in another system by comparing results of that system to the known results shown in FIG. 6. Fluorescent light source 74 and device 70 may include other spectral outputs.

In one embodiment, fluorescent light source 74 includes emits low-intensity light. In one embodiment, a low intensity fluorescent light source of the present invention emits light within device 70 in the range of about $10^4$ to about $10^{13}$ photons/second. For some imaging systems, a fluorescent light source 74 that emits flux in the range of about $10^6$ to about $10^{11}$ photons/second is suitable. Other light fluxes are permissible with the present invention. Photons/second is one unit of measure suitable to quantify the amount of light produced by light source 74. Other units of measure are known to one of skill in the art, such as Watts. For reference, the conversion of photons/second to Watts is 3.3 nanowatts equals about $10^{10}$ photons/second at 600 nm. In one embodiment, light source 74 emits light between about $10^{-15}$ to $10^{-6}$ watts of light. The amount of light produced by light source 74 refers to the light emitted within body 71—not necessarily the amount of light generated by a light source (such as an LED) that generates the light incident on the fluorescent light source 74.

The amount of fluorescent light source 74 and fluorophores contained therein may be adapted to provide these, and other, light ranges, as one of skill in the art will appreciate. In one embodiment, fluorescent light source 74 includes between about $10^{10}$ to about $10^{16}$ molecules of fluorophore.

In a specific embodiment, fluorescent light source 74 in cavity 85 includes between about $4\times10^{13}$ to about $2.5\times10^{15}$ molecules of FITC. Between about $1\times10^{11}$ to about $5\times10^{12}$ molecules of quantum dot 605 or quantum dot 800 is suitable for phantom device 70. In another specific embodiment, fluorescent light source 74 includes between about $2.4\times10^{13}$ to about $1.2\times10^{15}$ molecules of AlexaFluor™ 680 and/or between about $1\times10^{11}$ to about $5\times10^{12}$ molecules of AlexaFluor™ 750. Other ranges for each fluorophore may also be used.

Fluorescent light source 74 may also be designed and configured to produce a desired radiance from the surface of phantom device 70. Photons/second/centimeter squared/steradian are units of photon radiance on a surface. A desirable range for light emitted from light source 74 will depend on a number of factors such as the sensitivity and saturation of the camera used, the ability of the imaging box to seal light, level of internally generated light in the imaging box, imaging system parameters such as integration time, binning, and f-stop, etc. In one embodiment, a low intensity light source of the present invention emits light within device 70 in the range of about $10^3$ to about $10^{11}$ photons/second/centimeter squared/steradian. For some imaging systems, a low intensity light source 74 that emits light in the range of about $10^9$ to about $10^{10}$ photons/second/centimeter squared/steradian is suitable. In some cases, the intensity of light emitted from light source 74 may be determined according to the sensitivity of a camera used in the imaging system over a duration corresponding to saturation of the camera caused by light emitted from the light source 74. Saturation refers to the amount of light and time it takes for the camera, or the analog-to-digital converter associated with the camera, to reach its exposure capacity. For example, the saturation duration may range from about five seconds to about five minutes, depending on the rate of light emitted from the object. For phantom device 70, the output of low intensity light source 74 may be increased to expedite imaging when imaging occurs over an extended period of time.

Suitable levels of illumination from fluorescent light source 74 may also be described in terms of output power. In a specific embodiment, fluorescent light source 74 emits from about $10^{-15}$ to about $10^{-6}$ watts of light. This range relatively compares to the intensity light provided by a tumor within a small mammal.

Phantom device 70 is well suited for benchmarking and testing diffuse tomographic light imaging systems and software. The phantom device has other applications with a light imaging system, as will be described below with respect to FIG. 8.

FIGS. 7A and 7B illustrate an imaging system 10 configured to capture photographic, fluorescent and luminescent images suitable for use with phantom device 70. While testing will now be described with respect to imaging system 10, it is understood that phantom device 70 is well suited for use with other imaging systems.

Imaging system 10 may be used for imaging a low intensity light source, such as phantom device 70, luminescence from luciferase-expressing cells, fluorescence from fluorescing molecules, and the like. The low intensity light source may be included in any of a variety of living or non-living light-emitting samples. Non-living light-emitting samples may include calibration devices and phantom devices. Living light-emitting samples may include, for example, animals or plants containing light-emitting molecules, tissue culture plates containing living organisms, and multi-well plates (including 96, 384 and 864 well plates) containing living organisms. Animals may include any mammal, such as a mouse or rat containing luciferase-expressing cells.

System 10 finds wide use in imaging and research. The ability to track light-emitting cells in a small laboratory animal such as a mouse or rat opens up a wide range of applications in pharmaceutical and toxilogical research. These include in vivo monitoring of infectious diseases, tumor growth in metastases, transgene expression, compound toxicity, and viral infection or delivery systems for gene therapy. The ability to detect signals in real-time and in living animals means that the progression of a disease or biological process can be studied throughout an experiment with the same set of animals without a need to sacrifice for each data point.

Imaging system 10 comprises an imaging box 12 having a door 18 and inner walls 19 (FIG. 7B) that define an interior cavity 21 that is adapted to receive a light-emitting sample or phantom device 70 in which low intensity light is to be detected. Imaging box 12 is suitable for imaging including the capture of low intensity light on the order of individual photons, for example. Imaging box 12 is often referred to as "light-tight". That is, box 12 seals out essentially all of the external light from the ambient room from entering the box 12, and may include one or more seals that prevent light passage into the box when door 18 is closed. In a specific embodiment, door 18 comprises one or more light-tight features such as a double baffle seal, while the remainder of chamber 21 is configured to minimize any penetration of light into cavity 21.

Phantom device 70 is placed within box 12 for imaging by opening door 18, inserting the testing device in chamber 21, and closing door 18. Suitable imaging systems are available from Caliper Life Sciences from MountainView, Calif., and include the IVIS® Spectrum, IVIS® 3D Series, IVIS® 200 Series, IVIS® 100 Series, and IVIS® Lumina. Further description of a suitable imaging box 12 is provided in commonly owned pending patent application Ser. No. 09/905,668 entitled "3-D Imaging Apparatus for In-Vivo Representations", which is incorporated by reference herein in its entirety for all purposes. Although imaging system 10 is shown with a single cabinet design, other embodiments of the present invention include a disparate imaging box 12 and computer that includes processing system 28 and a dedicated display.

Imaging box 12 includes an upper housing 16 adapted to receive a camera 20 (FIG. 7B). A high sensitivity camera 20, e.g., an intensified or a charge-coupled device (CCD) camera, is mounted on top of upper housing 16 and positioned above imaging box 12. CCD camera 20 is capable of capturing luminescent, fluorescent, structured light and photographic (i.e., reflection based images) images of a living sample or phantom device placed within imaging box 12. One suitable camera includes a Spectral Instruments 620 Series as provided by Spectral Instruments of Tucson, Ariz. CCD camera 20 is cooled by a suitable source such as a refrigeration device that cycles a cryogenic fluid to cool the CCD camera via conduits that communicate the cooling fluid into channels 24. A suitable refrigeration device comprises the "CRYOTIGER" compressor, which can be obtained from IGC-APD Cryogenics Inc., Allentown, Pa. Other methods, such as liquid nitrogen, may be used to cool camera 20.

Imaging system 10 may also comprise a lens (not shown) that collects light from the specimen or phantom device and provides the light to the camera 20. A stage 25 forms the bottom floor of imaging chamber 21 and includes motors and controls that allow stage 25 to move up and down to vary the field of view 23 for camera 20. A multiple position filter wheel may also be provided to enable spectral imaging capability.

Imaging box 12 may also include one or more light emitting diodes on the top portion of chamber 21 to illuminate a sample during photographic image capture. Other features may include a gas anesthesia system and heated sample shelf to maintain an animal's body temperature during image capture and anesthesia.

FIG. 7B shows system 10 with the removal of a side panel for imaging box 12 to illustrate various electronics and processing components included in system 10. Imaging system 10 comprises image processing unit 26 and processing system 28. Image processing unit 26 optionally interfaces between camera 20 and processing system 28 and may assist with image data collection and video data processing. Processing system 28, which may be of any suitable type, comprises hardware including a processor 28a and one or more memory components such as random-access memory (RAM) 28b and read-only memory (ROM) 28c.

In one embodiment, imaging system 10 includes its own processor 28a and memory 28b and 28c. In another embodiment, processor 28a and memory 28b and 28c are included in an external computer, such as a desktop PC, that is electronically or digitally coupled to the imaging system 10. Processor 28a (also referred to as a central processing unit, or CPU) couples to storage devices including memory 28b and 28c. ROM 28c serves to transfer data and instructions uni-directionally to the CPU, while RAM 28b typically transfers data and instructions in a bi-directional manner. A fixed disk is also coupled bi-directionally to processor 28a; it provides additional data storage capacity and may also include any of the computer-readable media described below. The fixed disk may be used to store software, programs, imaging data and the like and is typically a secondary storage medium (such as a hard disk).

Processor 28a communicates with various components in imaging box 12. To provide communication with, and control of, one or more system 10 components, processing system 28 employs software stored in memory 28c that is configured to permit communication with and/or control of components in imaging box 12. For example, processing system 28 may include hardware and software configured to control camera 20. The processing hardware and software may include an I/O card, control logic for controlling camera 20. Components controlled by computer 28 may also include motors responsible for camera 20 focus, motors responsible for position control of a platform supporting the sample, a motor responsible for position control of a filter lens, f-stop, etc.

Processing system 28 may also interface with an external visual display (such as computer monitor) and input devices such as a keyboard and mouse. A graphical user interface that facilitates user interaction with imaging system 10 may also be stored on system 28, output on the visual display and receive user input from the keyboard and mouse. The graphical user interface allows a user to view imaging results and also acts an interface to control the imaging system 10. One suitable imaging software includes "LivingImage" as provided by Xenogen Corporation of Alameda, Calif.

Processing system 28 may comprise software, hardware or a combination thereof. System 28 may also include additional imaging hardware and software, test and calibration software, and image processing logic and instructions for processing information obtained by camera 20. For example, stored instructions run by processor 28a may include instructions for i) receiving image data corresponding to light emitted from a phantom device as described herein, ii) building a point, 2-D or 3-D digital representation of a light source internal to the phantom device using data included in the image, and iii) comparing a component of the digital representation to a known property for the light source or the test device.

Imaging system 10 employs a quantitative model that estimates the diffusion of photons in tissue. In one embodiment, the model processes in vivo image data and in order to spatially resolve a 3D representation of the size, shape, and location of the light emitting source. Typically, the tomographic model is stored as instructions in memory of processing system 28. Various diffusion and reconstruction models may be implemented by system 10 to represent photon propagation through a mammalian subject or a phantom device described herein. One suitable tomographic example of software that builds a digital representation of a light source internal to a mammalian sample or phantom device using data from one or more images is described in commonly owned and pending patent application Ser. No. 10/606,976 entitled "Method and Apparatus for 3-D Imaging of Internal Light Sources" and naming Brad Rice et al. as inventors. This application is incorporated by reference herein and its entirety for all purposes.

Phantom device 70 has multiple uses in an imaging system.

In one embodiment, a user may employ phantom device 70 to assess the performance of an imaging system. The assessment processes light output by the phantom device and compares a reconstruction of phantom device 70 and fluorescent light source 74 against known and expected results. More specifically, the assessment builds a digital representation of fluorescent light source 74 and/or phantom device 70 and compares one or more components of the digital representation against one or more known properties for the light source or the phantom device. By taking an image of the phantom device 70, or a portion thereof, and comparing the processed result with a known or expected result, the accuracy of the imaging system and its software imaging characteristics may be assessed, verified, and adapted if necessary.

In addition, phantom device 70 finds wide use for a low-light level imaging system when the system is not employed for imaging a living mammal. For example, phantom device 70 may be used when training new users or new purchasers of an imaging system, such as individuals in a research lab. Phantom device 70 thus finds particular service when new users are learning how to use an imaging system and complications associated with handling a living mammal are avoided.

Phantom device 70 may also be used to test hardware components in system 10 as required for routine calibration or verification of an imaging system. For example, components such as the camera, positioning system and lens may be routinely tested for health. In addition, phantom device 70 may be used upon system breakdown, such as when a filter may have cracked. In testing for diagnosis of an unknown breakdown, the imaging system comprises so many parts that use of a living mammal may be detrimental and test device 70 simplifies testing by reducing the number of unknowns.

Figure 8:
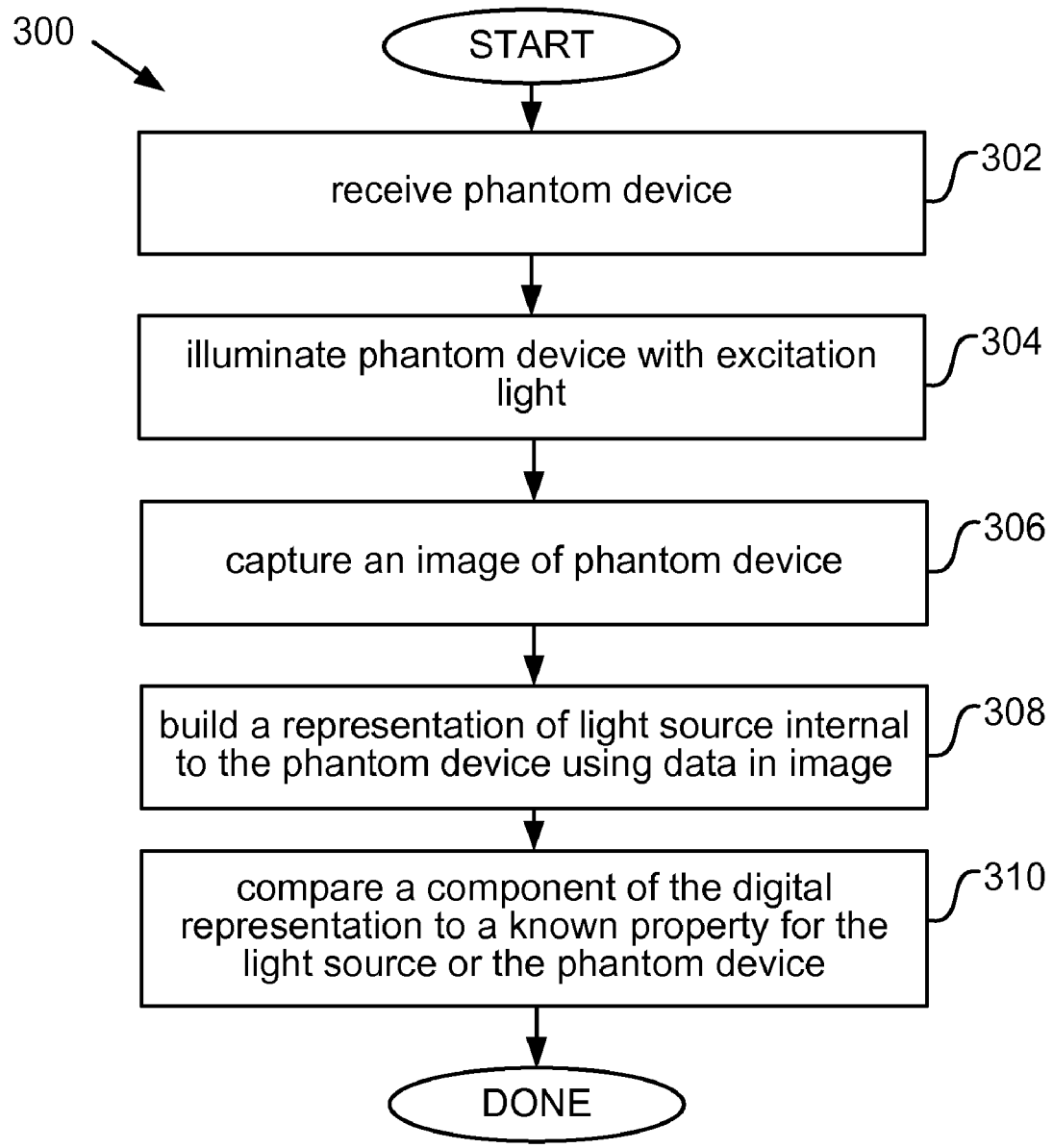
FIG. 8 illustrates a process flow for using a low-level light imaging system in accordance with one embodiment of the present invention.

FIG. 8 illustrates a process flow 300 for using a low-level light imaging system in accordance with one embodiment of the present invention. Process flow 300 assesses the performance of a low-level light imaging system by processing light output by a test device and quantitatively comparing a digital representation of the test device or a light source inside the phantom device against one or more known emission properties or characteristics for the phantom device or light source.

Process flow 300 begins by receiving a phantom device (302) in an imaging system, such as in the field of view for a camera included in a low-level light imaging system. Typically, a user places the phantom device in the internal cavity and initiates image capture via software. In response, the imaging system prepares the imaging system for image capture.

Fluorescence imaging is generally performed by illuminating the phantom device to excite fluorescence molecules in the internal fluorescent source, and then capturing an image of the phantom device, or a portion thereof, as it fluoresces using a camera. Fluorescent image capture proceeds by providing suitable excitation light onto the phantom device (304) with an illumination source. The excitation light should be large enough in magnitude to elicit a fluorescent response from the light source, but not too large so as to saturate autofluorescence of the tissue phantom body.

In response, minute amounts of light emitted from the "excited" fluorescent light source 74. Trans-illumination and/or epi-illumination may be used. Epi-illumination provides excitation light from a same side of the animal that the image is captured (e.g., incident light from above, and a camera above the mouse). Epi-illumination provides a faster survey of the entire animal, but may be subject to higher levels of autofluorescence. Epi-illumination avoids significant light attenuation through the mouse, and may help constrain volume elements near the camera-facing surface of the mouse. For example, the epi-illumination constraints may identify artifact voxels near the top surface, which are then removed by software. Trans-illumination provides excitation light from a side of the mouse opposite to the camera (e.g., incident light from below and a camera above), and provides lower levels of autofluorescence, which is useful for 3D tomographic reconstructions. Trans-illumination provides lower levels of autofluorescence and is useful for performing 3D tomographic reconstructions. Phantom device is suitable for both epi- and trans-illumination options in a fluorescence imaging system. In one embodiment where the mouse rests on a stage and the camera is above the mouse, epi-illumination uses excitation light that originates from above the mouse and stage, while trans-illumination uses excitation light that originates from below the mouse and stage. A transparent stage may be used to permit excitation light to pass through the stage.

Process flow 300 then captures an image of at least a portion of the phantom device 70 (306). The image may include the entire phantom device, or a portion of interest that has been zoomed in on. A user may initiate software included with the imaging system that controls components of the imaging system responsible for image capture. The software may also automatically implement various digital reconstruction and comparison steps described below (308 and 310). For example, the user may launch imaging and acquisition software on a computer associated with the imaging system that initializes the camera and carries out imaging and assessment automatically. According to stored instructions, the software may automatically select a desired stage position if a moveable stage is used, prepare the system for photographic or fluorescent image capture (e.g., turn on/off lights in the box), focus a lens, selectively position an appropriate fluorescent filter, select an incident fluorescent light supply, set an f-stop, transfer and store the image data, build a reconstruction, and compare the reconstruction results to known properties for the phantom device.

Image capture may include photographic and/or fluorescent image capture. For fluorescent image capture, software activates the camera to detect photons emitted from the phantom device, which usually corresponds to absolute units from the surface. The camera may capture the fluorescent image over a set period of time (up to several minutes). A photon signal produced by the camera is transferred to the image processing unit and/or computer and used to construct a fluorescent image of photon emission. A fluorescent image records fluorescence as a function of position. A photographic image may also be taken of the same sample to aid in position visualization of the luminescent data.

The image processing system then builds a 2-D or 3-D digital representation of a light source internal to the phantom device using data included in the image and a computer-implemented reconstruction model (308). In the case where scattering is large compared with absorption, such as red to near-infrared light passing through tissue or a phantom device that comprises an optical material configured to resemble tissue, the transport of light within the sample may be described by diffusion theory. In this case, the computer-implemented reconstruction model implements a diffusion model to build the fluorescent light source digital representation. One 3-D diffusion software implementation reconstructs light data internal to the phantom device surface based on the surface light image data. In this case, the image and surface light data is converted into photon density just below the phantom device surface, and this photon density is used to produce 3-D light data internal to the test device surface including the light source. A suitable example of software that builds a 3-D digital representation of a light source internal to a test device using data from one or more images is described in commonly owned and pending patent application Ser. No. 10/606,976. Other software algorithms that build a 3-D digital representation of a light source using a diffuse tomography assessment are also suitable for use with the present invention.

Building the digital representation for the light source may rely on assumptions or estimates of optical properties for the phantom device. For example, reconstructing the digital representation of the light source may employ an optical scattering representation for the optical material used in the phantom device and employ an optical absorption representation for the optical material at one or more wavelengths. For phantom device 70, these representations for the phantom device are stored in memory and provided to the reconstruction algorithm when needed.

The resulting digital representation of the fluorescent light source may include information that includes mathematical descriptions of: an estimated intensity of the fluorescent light source, an estimated location of the light source within the phantom device, an estimated size or shape of the light source, and/or spectral characteristics of the fluorescent light source. In one embodiment, the light source is reconstructed as a point. This expedites reconstruction and provides a simpler representation for the light source that includes flux and depth. A user may then readily read how deep and how strong the light source is within the test device. In another embodiment, the light source is reconstructed as a complex source characterized spatially in three dimensions. This reconstruction uses surface topography of the phantom device and produces a light source with 3-D information such as size and shape.

The image processing system then compares a component of the digital representation to a known property for the light source or the phantom device 70 (306). The known property for the fluorescent light source may comprise any optical or spatial characteristic that describes the light source. In some cases, the known property for the fluorescent light source may comprise: an intensity for the light source, a size, position of the light source (device may include multiple positions for the light source, as described above), a shape of the light source, and/or a spectral pattern for the light source. The known property for the phantom device may include any optical or spatial characteristic that describes the phantom device, or a portion thereof (such as spectrally separating the fluorescence of body 71 from removable member 150). The known property for the phantom device, or a portion thereof, may include: scattering properties for the optical material, a surface size for a surface of the phantom device, a location of the light source within the test device or relative to a fiducial mark disposed on the test device, and an absorption response for the optical material (e.g., a spectral absorption response at one or more frequencies). Process flow 300 presumes that optical properties—such as autofluorescence, scattering and/or absorption coefficients—for the phantom device are known in advance. For example, a manufacturer of the phantom device may measure the optical properties before providing the phantom device to a customer or user. The manufacturer may also characterize the light source intensity and spectrum in advance to facilitate comparison.

A second image of the phantom device may also be captured at another wavelength. Since the optical material in the phantom device will absorb different wavelengths from the light source to various degrees, images taken at a second wavelength will produce an image with a different light output for the phantom device. This is particularly useful for fluorescent light sources since their emission spectrum—and the transmission selectivity of body 71—varies with wavelength. A filter may restrict the light received by the camera to a desired spectral range. Alternatively, the filtration may be done in software. Capturing images at multiple wavelengths then provides multiple images and data points for the same phantom device and light source. This second image (or third, etc.) may then be processed to further assess the imaging software and provide more information for reconstruction and system assessment.

Process flow 300 thus benchmarks—or compares—calculated values output by software against known results the phantom device (310). For example, the comparison may reconstruct the 3-D position of the light source relative to a known position of the light source in the phantom device body (e.g., known from manufacturing) and then check the position of the light source generated in the reconstruction against the known location relative to the fiducial mark. Alternatively, the comparison may assess the reconstructed light source strength with the known strength.

Based on the comparison, the software may alter a parameter used in building the digital representation to increase reconstruction accuracy. For example, the optical scattering or optical absorption representation used in reconstructing the digital representation may be altered to attain a more accurate reconstruction. Other parameters used in the reconstruction, such as the resolution of the surface mesh, size of internal voxels, or the number of different wavelengths, can also be altered to affect the reconstruction. After the alteration, the image processing system may build a second digital representation of the light source using the altered parameter and the original image. Another comparison may ensue based on the second reconstruction. By imaging a test device whose performance according to a functioning imaging system is known, and altering one or more parameters used in reconstructing the digital representation, process flow 300 eventually produces validated software for the imaging system.

Figure 10:
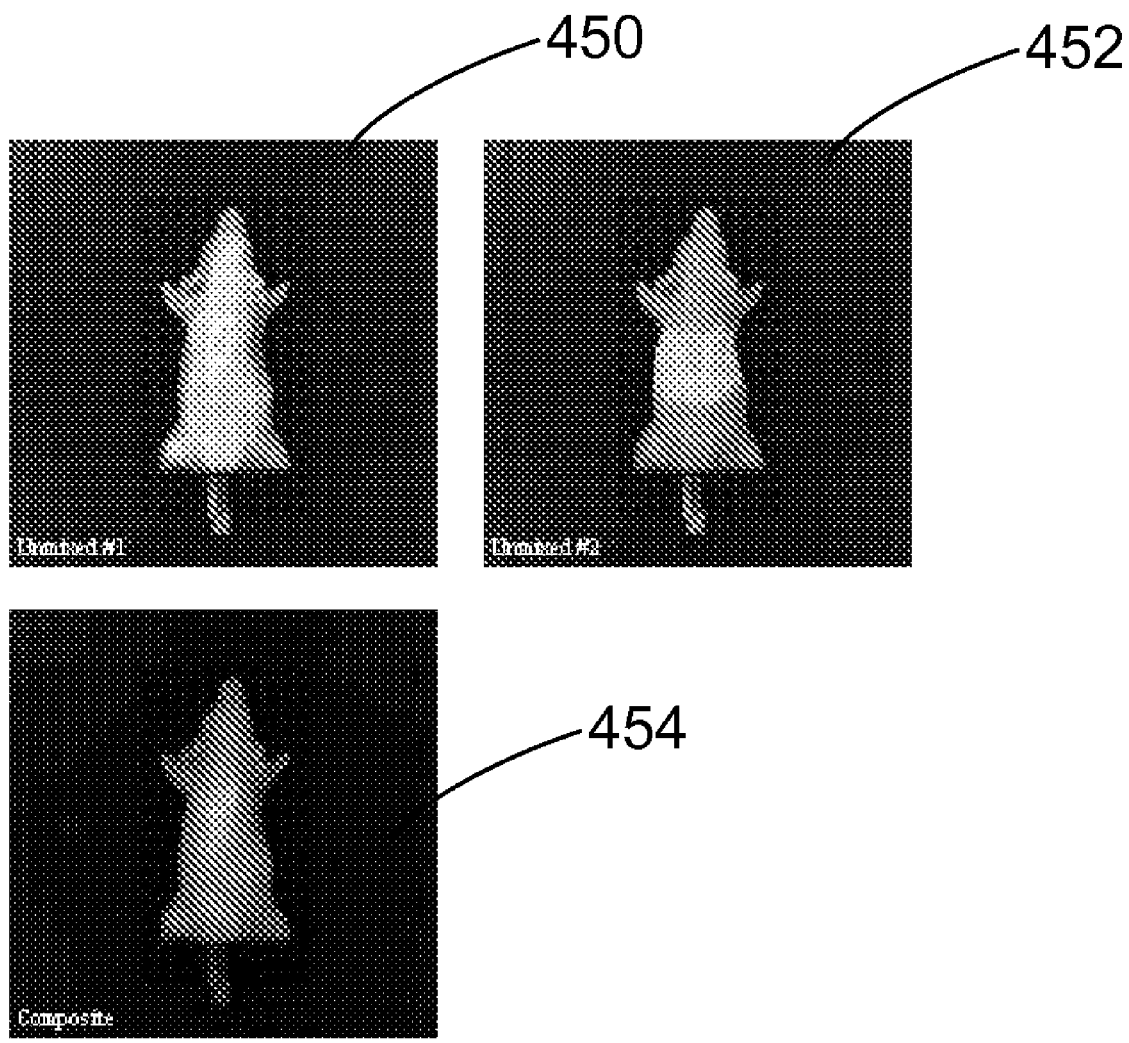
FIG. 10 shows sample images of the phantom device of FIG. 1 using the imaging system of FIG. 7A.

The comparison may also assess the spectral unmixing performance of an imaging system. In this case, image capture may occur multiple times, each through a different inlet filter, to gain a spectral profile image (see image 454 in FIG. 10). Software in the imaging system then separates the spectral contributions from the tissue or body 71 in phantom device 70. This is shown in FIG. 10 with three images: image 450 shows the autofluorescence of body 71 in phantom device 70; image 452 shows the fluorescence of light source 74; and image 454 shows the combination of images 450 and 452. A camera usually receives image data resembling image 454, and the autofluorescence of body 71 (or tissue in a real mammal) is to be removed before tomographic assessment of light source 74. The unmixing separates autofluorescence of body 71 from the fluorescence of light source 74. The spectra 134 and 130 in images in FIG. 6 correspond to image 450 and image 452, respectively. Since both a) the autofluorescence of body 71 and b) the fluorescence of light source 74 are known for phantom device 70, the results of the unmixing may be used to test the unmixing software for accuracy.

Multiple images may also be captured and processed to compare trans- and epi-fluorescent illumination for the phantom device and/or imaging system. For example, the comparison may evaluate the ratio of input signal to fluorescence gained from trans- and epi-fluorescent illumination to determine which was more effective for a position of the light source. Changing the position of the light source, e.g., using removable members 150 as described above, should change the trans- and epi-fluorescent illumination results, and the phantom device provides a tool to illustrate this. When training new users, this is particularly effective to teach when to do an epi-illumination fluorescent image or when to do a trans-illumination image (e.g., based on an estimated position of the light source in a real mammal).

The phantom device, and its known surface topography, may also be used to assess topographic processing in an imaging system.

Testing according to process flow 300 may be flexibly applied. In some cases, a manufacturer performs process flow 300 once during system set-up. Alternatively, process flow 300 may be repeated periodically during the operational life of the imaging system to verify the operational integrity of the software or system over time.

Figure 9:
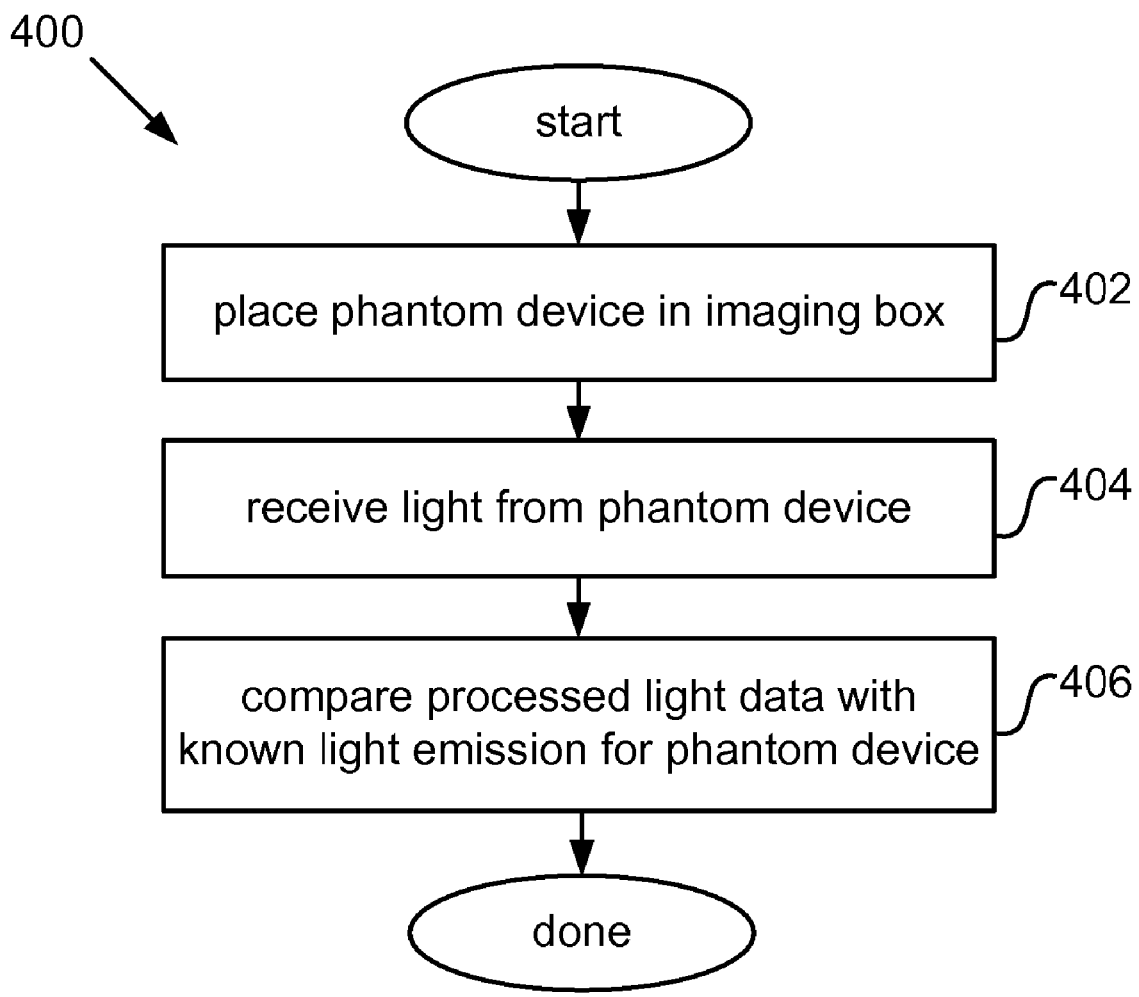
FIG. 9 illustrates a process flow for calibrating a low-level light imaging system in accordance with one embodiment of the present invention.

The phantom device 70 is also well suited for calibration of an imaging system. For example, process flow 300 may assume absolute calibration of an imaging system that converts counts on a camera or other photon detector to photons/sec/cm^2/steradian. This permits 3D reconstruction and derivation of light source strength in absolution units of flux (photons/sec). Depending on an application, light source strength can then be turned into more useful information, such as a molar concentration. For example, light source strength can be turned into a number of fluorescent cells provided the flux per cell is known. FIG. 9 illustrates a process flow 400 for calibrating a low-level light imaging system using phantom device 70 in accordance with one embodiment of the present invention.

Process flow 400 begins by placing the phantom device in an imaging box (402). As mentioned above, the phantom device includes a fluorescent light source of known intensity. A camera receives the light emitted from the calibration device (404) and provides a signal representative of the emitted light to an associated image processing system.

The image processing system processes the light emission data and compares the processed light data with known light emission for phantom device (406). In one embodiment, processing the light emitted from the phantom calibration device comprises integrating the amount of light in photons received over time.

Since the calibration device may be designed to emit a known value for light per unit time, a comparison of the number of photons received by the imaging system with the number of photons produced from the phantom device gives a user a simple comparison for assessing accuracy for the imaging system.

Embodiments of the present invention may relate to computer readable medium and computer storage products with a computer-readable medium that has computer code thereon for performing various computer-implemented operations described herein. The media and computer code may be those specially designed and constructed for the purposes of the present invention, or they may be of the kind well known and available to those having skill in the computer software arts. Examples of computer-readable media include, but are not limited to: magnetic media such as hard disks, optical media such as CD-ROMs; and hardware devices that are specially configured to store and execute program code, such as programmable logic devices (PLDs) and ROM and RAM devices. Examples of computer code include machine code, such as produced by a compiler, and files containing higher level code that are executed by a computer using an interpreter.

While this invention has been described in terms of several preferred embodiments, there are alterations, permutations, and equivalents which fall within the scope of this invention which have been omitted for brevity's sake. For example, although the present invention has primarily been discussed with respect to luminescent and fluorescent light imaging, phantom devices as described herein are also well-suited for use with other wavelength ranges and imaging modalities. It is therefore intended that the scope of the invention should be determined with reference to the appended claims.

What is claimed is:

1. A phantom device comprising:
   a body including one or more surfaces and an optical material designed to at least partially resemble the optical behavior of mammalian tissue; and
   a fluorescent light source disposed within the body and configured to emit fluorescent light from within the body, through the optical material and to the one or more surfaces.

2. The device of claim 1 wherein the fluorescent light source is stored in a cavity internal to the body.

3. The device of claim 2 further comprising a hole in the body sized to receive a removable member, wherein the cavity is formed in the removable member.

4. The device of claim 3 wherein the removable member has a cylindrical shape that includes the cavity.

5. The device of claim 2 wherein the removable member includes optical material that matches the optical material used in the body.

6. The device of claim 2 further comprising a second hole in the body sized to receive the removable member.

7. The device of claim 6 wherein the second hole has a different vertical position or a different lateral position than the first hole when the phantom device rests on a flat surface.

8. The device of claim 6 further comprising a second removable member configured to fit within the second hole, where the second removable member includes the optical material.

9. The device of claim 1 wherein the fluorescent light source includes a fluorophore.

10. The device of claim 9 wherein the fluorophore is suitable for use as a biological reporter in a mammal.

11. The device of claim 1 wherein the optical material is configured to resemble an autofluorescence spectrum of mammalian tissue.

12. The device of claim 1 wherein the fluorescent light source includes between about $10^{10}$ to about $10^{16}$ molecules of a fluorophore.

13. The device of claim 1 wherein surface topography of the body is designed to match the surface topography of a mammal.

14. The device of claim 1 wherein the optical material is substantially homogeneous.

15. The device of claim 1 wherein the optical material is configured to resemble an optical absorption property or optical scattering property of mammalian tissue.

16. A phantom device comprising:
    a body including one or more surfaces and an optical material designed to at least partially resemble the optical behavior of mammalian tissue;
    a hole in the body;
    a removable member including a cavity and shaped to fit in the hole; and
    a fluorescent light source disposed in the cavity and configured to emit fluorescent light from within the body when the removable member is in the hole.

17. The device of claim 16 wherein the removable member has a cylindrical shape that includes the cavity.

18. The device of claim 17 wherein the removable member includes optical material that matches the optical material used in the body.

19. The device of claim 16 further comprising a second hole in the body sized to receive the removable member.

20. The device of claim 19 wherein the second hole has a different height or a different lateral position than the first hole.

21. The device of claim 19 further comprising a second removable member configured to fit within the second hole, where the second removable member includes the optical material and does not include a cavity.

22. A method for testing a light imaging system, the method comprising:
    receiving a phantom device, the phantom device comprising a body including an optical material designed to at least partially resemble the optical behavior of mammalian tissue and a fluorescent light source internal to the body;
    illuminating the body with excitation light that causes the fluorescent light source to emit fluorescent light;
    capturing an image of at least a portion of a phantom device;
    building a digital representation of the fluorescent light source using data included in the image; and
    comparing a component of the digital representation to a known property for the fluorescent light source or the phantom device.

23. The method of claim 22 further comprising spectrally unmixing the image to produce a) a digital representation of the fluorescent light source and b) a digital representation of autofluorescence from the body.

24. The method of claim 23 wherein the optical material is configured to resemble an autofluorescence of mammalian tissue.

25. The method of claim 22 wherein the incident light is provided from below the body.

26. The method of claim 22 wherein the incident light is provided from above the body.

27. The method of claim 22 further comprising illuminating the body with second excitation light that causes the fluorescent light source to emit fluorescent light, wherein the first excitation light is provided from below the body and the second excitation light is provided from above the body.

28. The method of claim 27 further comprising:
    capturing a second image of at least the portion of a phantom device;
    building a second digital representation of the fluorescent light source using data included in the second image; and
    comparing a component of the first digital representation to a component of the second digital representation for the fluorescent light source or the phantom device.

29. The method of claim 22 further comprising assessing performance of the light imaging system using the comparison.

30. The method of claim 22 further comprising calibrating the light imaging system using the comparison.

31. The method of claim 30 wherein the fluorescent light source includes between about $10^{10}$ to about $10^{16}$ molecules of a fluorophore.

32. The method of claim 22 wherein the known property for the light source comprises one of: intensity for the light source, a size of the light source, and a spectral pattern for the light source.

33. The method of claim 22 wherein the known property for the phantom device comprises one of: a surface size for a surface of the phantom device, a location of the light source within the phantom device, and a spectral response for the optical material.

34. The method of claim 22 wherein the component comprises one of: a flux from a surface of the phantom device, an estimated intensity of the light source, an estimated location of the light source within the phantom device, and an estimated size of the light source.

35. A computer readable medium including instructions for testing a light imaging system, the instructions comprising:
    instructions for capturing an image of at least a portion of a phantom device, said phantom device having a body including one or more surfaces and an optical material designed to at least partially resemble the optical behavior of mammalian tissue, and also a fluorescent light source disposed within the body and configured to emit fluorescent light from within the body, through the optical material and to the one or more surfaces;
    instructions for building a digital representation of the fluorescent light source using data included in the image; and
    instructions for comparing a component of the digital representation to a known property for the fluorescent light source or the phantom device.

* * * * *